(12) United States Patent
Moreau

(10) Patent No.: US 8,796,265 B2
(45) Date of Patent: Aug. 5, 2014

(54) ANTI-INFECTIVE SOLUTION COMPRISING A COMPOUND OF PYRIDO(3,2,1-IJ)-BENZOXADIAZINE TYPE

(75) Inventor: Marinette Moreau, Saint-Germain (FR)

(73) Assignee: SA Vetoquinol (FR)

( * ) Notice: Subject to any disclaimer, the term of this patent is extended or adjusted under 35 U.S.C. 154(b) by 1116 days.

(21) Appl. No.: 12/161,827

(22) PCT Filed: Jan. 24, 2007

(86) PCT No.: PCT/FR2007/050682
§ 371 (c)(1),
(2), (4) Date: Sep. 9, 2008

(87) PCT Pub. No.: WO2007/085760
PCT Pub. Date: Aug. 2, 2007

(65) Prior Publication Data
US 2010/0280022 A1    Nov. 4, 2010

(30) Foreign Application Priority Data

Jan. 24, 2006  (FR) ...................... 06 50246

(51) Int. Cl.
*A61K 31/5395* (2006.01)
*A61P 31/00* (2006.01)
*A61K 9/00* (2006.01)

(52) U.S. Cl.
CPC ........... *A61K 9/0019* (2013.01); *A61K 31/5395* (2013.01)
USPC ...................... 514/229.2; 514/253.08; 544/66

(58) Field of Classification Search
CPC ............. A61K 31/5395; A61K 9/0019; C07D 498/06; A23K 1/1615
USPC .............................. 514/229.2, 253.08; 544/66
See application file for complete search history.

(56) References Cited

U.S. PATENT DOCUMENTS

| | | | |
|---|---|---|---|
| 4,801,584 A | 1/1989 | Yokose et al. |
| 5,808,076 A | 9/1998 | Vetter et al. |
| 5,998,418 A | 12/1999 | Bonse et al. |
| 6,103,716 A | 8/2000 | Dorgan et al. |

FOREIGN PATENT DOCUMENTS

| | | |
|---|---|---|
| EP | 0 259 804 A2 | 3/1988 |
| EP | 0 868 183 | 10/1998 |
| WO | WO 97/23217 A1 | 7/1997 |
| WO | 2005/018641 | 3/2005 |

OTHER PUBLICATIONS

Vetoquinol AG, Sep. 2005, XP-002444299.

*Primary Examiner* — Savitha Rao
(74) *Attorney, Agent, or Firm* — DLA Piper LLP (US)

(57) ABSTRACT

An anti-infection solution including (i) from 10% to 30% by weight with respect to the total volume of the solution of at least one compound of Formula (I):

Formula (I)

wherein: X represents a hydrogen or halogen atom or a hydroxy function, R1 represents: a 1-piperazinyl radical, which may be substituted in position 4 by a methyl, acetyl or 4-aminobenzyl group; a morpholino radical: a 1-pyrrolidinyl radical substituted in position 3 by a chlorine atom or by an amino, aminomethyl, (methylamino) methyl, (ethylamino) methyl or methoxy group; a 1-imidazolyl radical that can be substituted in position 4 by the methyl group, or a 1-piperidyl radical substituted in position 4 by a hydroxy or methoxy group, and R2 represents an alkyl radical, linear, branched or ring, including 1 to 10 carbon atoms, or at least one of its pharmaceutically acceptable salts, (ii) benzyl alcohol as a stabilizing agent, and at least one stabilizing agent, and (iii) at least one solubilization agent selected from the group consisting of carbolic acids and their esters, in a pharmaceutically acceptable carrier.

11 Claims, No Drawings

ANTI-INFECTIVE SOLUTION COMPRISING A COMPOUND OF PYRIDO(3,2,1-IJ)-BENZOXADIAZINE TYPE

RELATED APPLICATION

This is a §371 of International Application No. PCT/FR2007/050682, with an international filing date of Jan. 24, 2007 (WO 2007/085760 A2, published Aug. 2, 2007), which is based on French Patent Application No. 06/50246, filed Jan. 24, 2006.

TECHNICAL FIELD

This disclosure concerns anti-infection solutions intended to treat animals, more precisely an anti-infection solution comprising at least one pyrido(3,2,1-ij)-benzoxadiazine compound, and in particular a concentrated solution.

BACKGROUND

Among livestock, such as cattle, pigs, goats, sheep, poultry and/or horses, as well as in pets, the administration, in particular by injection, of products for therapeutic, prophylactic or metaphylactic purposes for anti-infection purposes is frequent.

The volume of product administered parenterally and the number of injection sites are important criteria in the choice of a formulation. One objective of producing a concentrated formula is to reduce the volume and/or the number of administrations, in particular with a view to reducing, for livestock, the muscular areas not able to be processed in the abattoir. Another important criterion, which may also be taken into account in the production of concentrated formulae, is the local tolerance, at the injection site, in particular for reducing losses at the abattoir.

However, some anti-infection products, for example marbofloxacin, have low solubility in water. This may lead to using technologies for increasing their solubility, such as salification, the use of complexes more soluble than the molecule itself, for example in combination with a cyclodextrin, pH modifiers, dispersed systems (emulsions, liposomes, vector systems), or the addition of adjuvants such as organic solvents, co-solvents or surfactants.

However, the techniques mentioned above may have very relative efficacy compared with certain specific compounds.

Among the solutions marketed, stable solutions containing up to 10% marbofloxacin can be cited. However, for certain therapeutic, prophylactic or metaphylactic indications, in particular in livestock, the therapeutic dose is high. Thus the use of solutions currently marketed requires the administration of large injection volumes, in particular greater than or equal to 40 ml, distributed in several injection sites. These conditions may lead to problems of tolerance.

EP 0 868 183 describes concentrated pharmaceutical aqueous solutions of danofloxacin comprising metallic salts, the tolerance of which, at the injection site, is said to be improved.

However, this type of formulation, previously prescribed for tetracyclins, may prove not to be applicable to or in any case not sufficiently effective with respect to every type of molecule, in particular with regard to certain quinolones.

However, for various reasons, including the improvement of animal wellbeing, a saving in time and/or improvement in meat yield, it may be desirable to reduce the volume of product administered parenterally or the number of injection sites and/or to improve the tolerance.

There therefore still exists a need for concentrated formulae of anti-infection compounds, in particular of the quinolone type, making it possible to reduce the volume or the number of administrations and/or having improved tolerance, thus being able, for livestock, to reduce the unusable muscular areas.

SUMMARY

I provide an anti-infection solution comprising: (i) from 10% to 30% by weight with respect to the total volume of the solution of at least one compound of Formula (I):

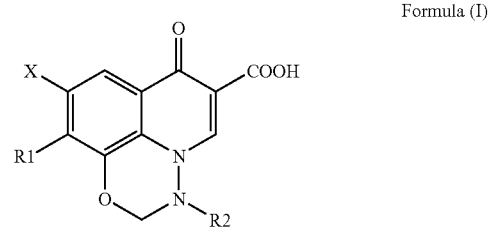

Formula (I)

wherein: X represents a hydrogen or halogen atom or a hydroxy function, R1 represents: a 1-piperazinyl radical, which may be substituted in position 4 by a methyl, acetyl or 4-aminobenzyl group; a morpholino radical: a 1-pyrrolidinyl radical substituted in position 3 by a chlorine atom or by an amino, aminomethyl, (methylamino) methyl, (ethylamino) methyl or methoxy group; a 1-imidazolyl radical that can be substituted in position 4 by the methyl group, or a 1-piperidyl radical substituted in position 4 by a hydroxy or methoxy group, and R2 represents an alkyl radical, linear, branched or ring, comprising 1 to 10 carbon atoms, or at least one of its pharmaceutically acceptable salts, (ii) benzyl alcohol as a stabilizing agent, and (iii) at least one solubilization agent selected from the group consisting of carbolic acids and their esters, in a pharmaceutically acceptable carrier.

I also provide an anti-infection medication including the solution.

I further provide a method of treating or preventing infections in animals including administering a therapeutically effective amount of the solution.

DETAILED DESCRIPTION

I provide a solution comprising 10% to 30% by weight with respect to the total volume of solution of at least one compound of the pyrido(3,2,1-ij)-benzoxadiazine type, or at least one of its pharmaceutically acceptable salts, and at least solubilization agent or solubilizing agent, in a pharmaceutically acceptable carrier.

"Compound of the pyrido(3,2,1-ij)-benzoxadiazine type" means a compound complying with the following Formula (I):

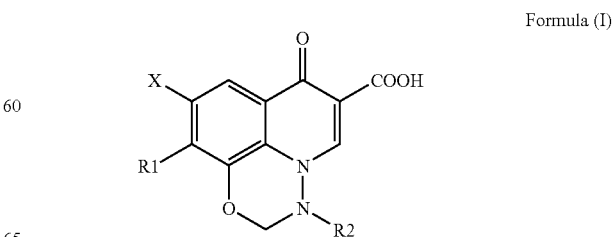

Formula (I)

in which:
X represents a hydrogen or halogen atom or a hydroxy function, and in particular a fluorine atom,
R1 represents:
 a 1-piperazinyl radical, which may be substituted in position 4 by a methyl, acetyl or 4-aminobenzyl group;
 a morpholino radical:
  a 1-pyrrolidinyl radical substituted in position 3 by a chlorine atom or by an amino, aminomethyl, (methylamino) methyl, (ethylamino) methyl or methoxy group;
  a 1-imidazolyl radical that can be substituted in position 4 by the methyl group, or
  a 1-piperidyl radical substituted in position 4 by a hydroxy or methoxy group, and
R2 represents an alkyl radical, linear, branched or ring, comprising 1 to 10 carbon atoms, in particular a methyl group, and
 its pharmaceutically acceptable salts.

The compound of the pyrido(3,2,1-ij)-benzoxadiazine type can in particular comply with Formula (I) in which R1 represents a 1-piperazinyl radical substituted in position 4 by a methyl group, R2 represents a methyl group and X represents a fluorine atom. This compound can in particular be obtained by the methods described in EP 0 259 804. This compound complies in particular with the International Common Denomination of marbofloxacin.

The solution can comprise a proportion of compound of the pyrido(3,2,1-ij)-benzoxadiazine type ranging from 10% to 30% by weight, especially ranging from 11% to 28% by weight, in particular ranging from 12% to 27% by weight, quite especially ranging from 13% to 25% by weight, even more especially ranging from 14% to 23% by weight or even ranging from 15% to 20% by weight with respect to the total volume of the solution.

The solution comprises at least one solubilization agent. This solubilization agent can form a complex with the compound of the pyrido(3,2,1-ij)-benzoxadiazine type. In particular when this solubilization agent is an acid, it can form a salt with the compound of the pyrido(3,2,1-ij)-benzoxadiazine type.

The formation of such complexes may make it possible to improve the solubilization of the compound of the pyrido(3,2,1-ij)-benzoxadiazine type in solution, in particular in aqueous solution.

Among the solubilization agents the following can be cited:
 mineral acids, in particular hydrochloric, hydrobromic, sulphuric, phosphoric and nitric acid, and
 organic acids, such as carboxylic acids, sulphonic acids and phosphonic acids; in particular formic, acetic, proprionic, succinic, glycolic, lactic or polylactic, malic, tartric, citric, ascorbic, maleic, hydroxymaleic, phenylacetic, benzoic, 4-aminobenzoic, anthranilic, 4-hydroxybenzoic, salicylic, aminosalicylic, nicotinic, methane sulphonic, ethane sulphonic, hydroxyethane sulphonic, benzene sulphonic and p-toluenesulphonic acids; polycarboxylic acids, such as gluconic acid, glucuronic acid, galacturonic acid, isophthalic acid and lactobionic acid; amino acids, such as aspartic and glutamic acid, methionine, tryptophan, lysine and arganine; esters thereof, among which gluconolactone can be cited, and salts thereof, and
mixtures thereof.

Among the solubilization agents of the compounds of the pyrido(3,2,1-ij)-benzoxadiazine type, and in particular marbofloxacin, lactic acid, gluconic acid and gluconolactone can be cited in particular.

The solution may comprise a solubilization agent content ranging from 4% to 58% by weight, especially 5% to 35% by weight, in particular ranging from 6% to 25% by weight, or even ranging from 7% to 20% by weight with respect to the total volume of the solution.

In particular, the solution comprises a mole ratio between solubilization agent and compound of pyrido(3,2,1-ij)-benzoxadiazine type ranging from 0.9 to 4, especially from 1 to 3, and in particular from 1.1 to 2.4.

The solution may comprise a solubilization agent content such that the pH of the solution ranges from 2 to 7, in particular from 2.8 to 5.

The solutions described above may have limited stability, in particular when they comprise a high concentration of compound of the pyrido(3,2,1-ij)-benzoxadiazine type and a low concentration of solubilization agent.

I discovered that it was possible to improve the feasibility of certain concentrated solutions and/or their stability by adding at least one solubilizing agent and/or at least one stabilizing agent.

The stabilizing agent can be chosen from the group comprising alcohols, propylene glycols, polyethylene glycol, glycerine. More particularly, the stabilizing agent is an alcohol, in particular aromatic, alkyl, arylalkyl or alkylaryl, in particular comprising 5 to 15 carbon atoms, and especially benzyl alcohol and its derivatives.

"Derivative of benzyl alcohol" means compounds complying with Formula (II):

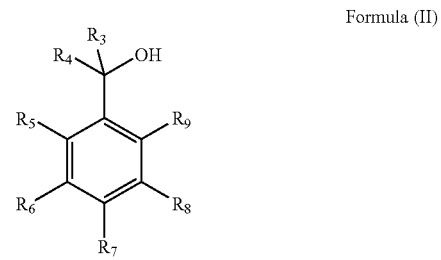

Formula (II)

in which $R_3$, $R_4$, $R_5$, $R_6$, $R_7$, $R_8$ and $R_9$ represent independently a hydrogen, atom halogen, an alcohol, ether or amine function, possibly substituted, a thioether, ester or amine function, possibly substituted, or an alkyl, aryl, aralkyl, alkaryl radical.

In particular, the solution comprises a stabilizing agent content ranging from 0.2% to 20% by weight, especially 0.3% to 10% by weight, in particular 0.4% to 5% by weight, and especially 0.5% to 3% by weight with respect to the total volume of the solution.

Moreover, the solution may comprise a mole ratio between stabilizing agent and compound of the pyrido(3,2,1-ij)-benzoxadiazine type ranging from 0.02 to 7, especially from 0.05 to 5, in particular from 0.1 to 1.5, or even 0.2 to 1.

In particular, the solutions may comprises a mole ratio between solubilization and stabilizing agent ranging from 1 to 15, especially from 1.5 to 10, in particular from 2 to 8, or event 2.5 to 7.

The solutions can also comprise at least one additive, in particular chosen from the group comprising:
 a solvent, for example chosen from non-aqueous solvents able to be used parenterally, i.e., solvents non-miscible with water, for example vegetable oils or ethyl oleate, or solvents miscible with water, in particular alcohols, such as ethanol; amides, such as N,N dimethylacetamide; polyol esters, such as polyglucosated glyceride; ethers, such as dimethyl-1,3-dioxolane-4-methanol, diethylene glycol monoethylic ether, formal glycerol, polyethylene glycol, in particular PEG 300 and PEG 400; polyols, such as glycerol or propylene glycol; dimethylsulphoxide; 2-pyrrolidone; or a mixture of these, a surfactant, for example non-ionic, anionic, cationic, or a mixture of surfactants, and especially a non-ionic surfactant;

a chelating agent, for example EDTA, a preservative, in particular an antioxidant, or an antimicrobial, and a mixture of these.

The solution may in particular be an aqueous solution.

The pH of the solution may range from 2 to 7, in particular 2.8 to 5.

In particular, the solution is in the form of an injectable solution, in particular by intramuscular, subcutaneous, intraperitoneal and/or intravenous route. The solution may also be an infusion or perfusion. This solution may be intended for so-called livestock, such as sheep, cattle, pigs, goats, horses and/or poultry, and/or pets, such as dogs and cats.

In particular, the solution has a viscosity ranging from $10^{-4}$ to $10^{-2}$, in particular $10^{-3}$ to $5.10^{-3}$ Pa·s at 20° C.

The solution may be clear, in particular may not comprise any particles in suspension.

I also provide for the use of at least one compound of the pyrido(3,2,1-ij)-benzoxadiazine type as described above in the preparation of a solution intended to treat or prevent infections, in particular in animals, the compound of the pyrido(3,2,1-ij)-benzoxadiazine type being present in a proportion ranging from 10% to 30% by weight, especially from 11% to 28% by weight, or even from 12% to 27% by weight, in particular from 13% to 25% by weight, especially from 14% to 23% by weight or even from 15% to 20% by weight with respect to the total volume of the solution.

I further provide for the use of a solution of a medication intended to treat or prevent infections, in particular, in animals.

Among infections able to be treated, infections of the respiratory system, of the reproduction system, of the urinary system, of the digestive system, of the locomotive or cardiovascular system, of the cutaneous type, otitis ophthalmic, in particular in animals, can be mentioned.

I still further provide a method of treatment, prevention and metaphylaxis of infections in animals. The treatment method can comprise the injection of 0.01 to 0.05 ml of concentrated solution per kg, in particular 0.01 to 0.01 ml/kg of animal to be treated. In particular the treatment may comprise a single injection at a single point.

For example, for a 300 kg animal, the treatment of a respiratory infection can be carried out with "Marbocyl S" with a volume of 24 ml, administered at two injection points, and with the solution with a volume of 15 ml, injected at 1 single point.

"Treatment," within the meaning of the disclosure, means the treatment in itself, but also prophylaxis and metaphylaxis.

I yet further provide for the use of at least one compound chosen from alcohols, propylene glycols, polyethylene glycols and glycerine, as an agent stabilizing a solution of a compound of Formula (I). More particularly, the stabilizing agent is an alcohol, especially aromatic, alkyl, arylalkyl or alkylaryl, in particular comprising 5 to 15 carbon atoms, and especially benzyl alcohol and its derivatives, as a stabilizing agent for a solution comprising at least one compound of Formula (I), in particular at a high concentration, in particular greater than 10% by weight with respect to the total volume of the solution, and possibly a solubilization agent.

The compositions concerns the use of at least one compound chosen from:

mineral acids, in particular hydrochloric, hydrobromic, sulphuric, phosphoric and nitric acid, and organic acids, such as carboxylic acids, sulphonic acids and phosphonic acids; in particular formic, acetic, proprionic, succinic, glycolic, lactic or polylactic, malic, tartric, citric, ascorbic, maleic, hydroxymaleic, phenylacetic, benzoic, 4-aminobenzoic, anthranilic, 4-hydroxybenzoic, salicylic, aminosalicylic, nicotinic, methane sulphonic, ethane sulphonic, hydroxyethane sulphonic, benzene sulphonic and p-toluenesulphonic acids; polycarboxylic acids, such as gluconic acid, glucuronic acid, galacturonic acid, isophthalic acid and lactobionic acid; amino acids, such as aspartic and glutamic acid, methionine, tryptophan, lysine and arganine; esters thereof, among which gluconolactone can be cited, and salts thereof, and mixtures thereof, as an agent for solubilizing a solution of a compound of Formula (I), in particular at a high concentration, in particular greater than 10% by weight with respect to the total volume of the solution, possibly also comprising a stabilizing agent.

The use of a stabilizing agent, and in particular benzyl alcohol, may also enable solutions with a high concentration of compound of Formula (I), in particular marbofloxacin, and comprising at least one solubilization agent, in particular gluconolactone, to have a pH and/or an osmolarity that is less compared with solutions comprising an equivalent concentration of compound of Formula (I) and possibly a solubilization agent. This may in particular enable concentrated solutions comprising at least one compound of Formula (I), a solubilization agent and a stabilizing agent to have a pH and/or an osmolarity close to less concentrated compositions, in particular in terms of compound of Formula (I) and/or solubilization agent. This is related to the presence of a stabilizing agent that may make it possible to use less solubilization agent.

In other words, the addition of stabilizing agent also makes possible the manufacture of certain solutions with a very high concentration of compound of Formula (I) adapted to injection, which would not be so, or only with difficulty, without the addition of this agent. Effectively, the stabilizing effect may increase with the proportion of stabilizing agent.

In particular, I provide for the use of the association firstly of benzyl alcohol and secondly of lactic acid, gluconic acid and/or gluconolactone as a solubilizing and stabilizing agent for a solution of compound of Formula (I), in particular at a concentration higher than 10%, especially higher than 11%, in particular higher than 12% by weight, especially higher than 13% by weight, or even higher than 14% by weight with respect to the volume of the solution.

The following examples are given by way of illustration and can under no circumstances serve to limit the scope of this disclosure or the appended claims.

EXAMPLES

Example 1

The solutions described in Table 1 below were prepared:

|  | Batch 1 | Reference |
| --- | --- | --- |
| Marbofloxacin (in grams) | 15.00 | 10.00 |
| Gluconolactone (in grams) | 8.11 | 8.00 |
| Demineralized water qsp | 100 ml | 100 ml |

Pigs weighing 70-80 kg received a single injection of reference solution in the right neck and a solution of batch 1 in the left neck, by intramuscular route, at a dose of 8 mg/kg. The local tolerance (postmortem lesions) were examined one week after administration.

The injection with batch 1 has a lesion volume of approximately 9 cm$^3$ while the injection with the reference shows a lesion volume of 32 cm$^3$.

This demonstrates better local tolerance of the concentrated marbofloxacin solution, compared with the reference solution.

Example 2

The following batches were prepared:

|  | Batch 1 | Batch 2 | Batch 3 | Batch 4 |
| --- | --- | --- | --- | --- |
| Marbofloxacin | 20.00 g | 20.00 g | 20.00 g | 20.00 g |
| Gluconolactone | 19.00 g | 19.00 g | 17.00 g | 17.00 g |
| Benzyl alcohol | — | 2.00 g | — | 2.00 g |
| Demineralized water | qsp 100 ml | qsp 100 ml | qsp 100 ml | qsp 100 ml |
| Stability cold | 24 hours | >7 days* | 24 hours | >7 days* |

*After 7 days, no precipitate was observed.

"Stability cold" means the time for which a precipitate forms when the batches are left immobile between +4° C. and +8° C.

This demonstrates clearly an improvement in the stability of the solutions.

The invention claimed is:

1. An injectable anti-infection solution comprising:
   (i) from 10% to 30% by weight with respect to the total volume of the solution of compound of Formula (I):

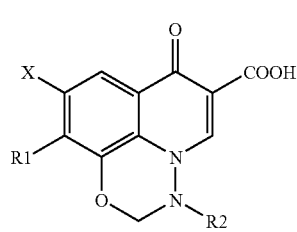

Formula (I)

Wherein:

R1 represents a 1-piperazinyl radical substituted in position 4 by a methyl group, R2 represents a methyl group and X represents a fluorine atom or at least one of its pharmaceutically acceptable salts, (ii) benzyl alcohol as a stabilizing agent, and (iii) at least one solubilization agent selected from the group consisting of organic acids and their esters, in a pharmaceutically acceptable carrier.

2. The solution according to claim 1, which comprises a proportion of compound of formula (I) ranging from 11% to 20% by weight with respect to the total volume of the solution.

3. The solution according to claim 1, wherein the solubilization agent is selected from the group consisting of lactic acid, gluconic acid and gluconolactone.

4. The solution according to claim 1, which comprises a proportion of solubilization agent ranging from 4% to 58% by weight, with respect to the total volume of the solution.

5. The solution according to claim 1, wherein the mole ratio between solubilization agent and compound of formula (I) ranges from 0.9 to 4.

6. The solution according to claim 1, in which the solubilization agent is present in a proportion such that the pH of the solution ranges from 2 to 7.

7. The solution according to claim 1, which comprises a proportion of stabilizing agent ranging from 0.2 to 20% by weight with respect to the total volume of the solution.

8. The solution according to claim 1, which comprises a mole ratio between stabilizing agent and compound of formula (I) ranging from 0.02 to 7.

9. The solution according to claim 1, which has a pH ranging from 2 to 7.

10. An anti-infection medication comprising the solution according to claim 1.

11. A method of treating or preventing infections in animals comprising administering a therapeutically effective amount of the solution according to claim 1.

* * * * *